PATENT

(12) United States Patent
Singh et al.

(10) Patent No.: US 8,481,596 B2
(45) Date of Patent: Jul. 9, 2013

(54) POLYMOMORPH OF DESVENLAFAXINE BENZOATE

(75) Inventors: Gurvinder Pal Singh, Pune (IN); Dabeer Rauf Karnalkar, Pune (IN); Hemraj Mahadeorao Lande, Pune (IN); Girij Pal Singh, Pune (IN)

(73) Assignee: Lupin Limited, Mumbai, Maharashtra (IN)

( * ) Notice: Subject to any disclaimer, the term of this patent is extended or adjusted under 35 U.S.C. 154(b) by 117 days.

(21) Appl. No.: 13/238,953

(22) Filed: Sep. 21, 2011

(65) Prior Publication Data
US 2012/0316238 A1 Dec. 13, 2012

(30) Foreign Application Priority Data

Jun. 8, 2011 (IN) .............................. 761/KOL/2011

(51) Int. Cl.
*A61K 31/205* (2006.01)
*C07C 63/08* (2006.01)

(52) U.S. Cl.
CPC ............... *A61K 31/205* (2013.01); *C07C 63/08* (2013.01)

USPC .......................................... 514/555; 562/493

(58) Field of Classification Search
CPC ............................... A61K 31/205; C07C 63/08
See application file for complete search history.

(56) References Cited

U.S. PATENT DOCUMENTS

| 4,535,186 | A | 8/1985 | Husbands et al. |
| 6,673,838 | B2 | 1/2004 | Hadfield et al. |
| 7,001,920 | B2 | 2/2006 | Hadfield et al. |
| 2011/0046231 | A1* | 2/2011 | Sebastian et al. ............. 514/653 |

FOREIGN PATENT DOCUMENTS

WO    WO 2009/053840 A2    4/2009

\* cited by examiner

*Primary Examiner* — Paul A Zucker
(74) *Attorney, Agent, or Firm* — Merchant & Gould P.C.

(57) ABSTRACT

The present invention relates to a novel crystalline form L of (±)-desvenlafaxine benzoate and process for the preparing of the same. Further, the present invention also relates to pharmaceutical composition of novel crystalline form L of desvenlafaxine benzoate and one or more pharmaceutically acceptable excipient.

10 Claims, 4 Drawing Sheets

POLYMOMORPH OF DESVENLAFAXINE BENZOATE

This application claims benefit of Serial No. 761/KOL/2011, filed 8 Jun. 2011 in India and which application is incorporated herein by reference. A claim of priority, to the extent appropriate is made.

TECHNICAL FIELD OF THE INVENTION

The present invention provides highly reproducible novel crystalline form L of (±)-desvenlafaxine benzoate and process for preparing the same. Further, the present invention provides pharmaceutical composition of novel crystalline form L of desvenlafaxine benzoate and one or more pharmaceutically acceptable excipient.

BACKGROUND OF THE INVENTION

Desvenlafaxine is chemically known as 4-[2-(dimethylamino)-1-(1-hydroxycyclohexyl)ethyl]phenol. It is a major metabolite of venlafaxine and has been shown to inhibit norepinephrine and serotonin reuptake. Desvenlafaxine, which can also be referred to as O-desmethylvenlafaxine, is represented by the following structural formula:

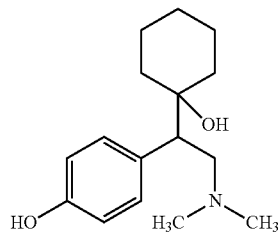 [SMILES: CN(C)CC(c1ccc(O)cc1)C1(O)CCCCC1]

Desvenlafaxine is first disclosed in U.S. Pat. No. 4,535,186. It describes the process for preparation of desvenlafaxine and its salts with pharmaceutically acceptable organic or inorganic acids like hydrochloric acid, hydrobromic acid, maleic acid, fumaric acid, succinic acid, sulfuric acid, phosphoric acid, tartaric acid, acetic acid, citric acid and oxalic acid.

WO 2009/053840 discloses oxalate, lactate and benzoate salts of desvenlafaxine along with their process of preparation and polymorphic forms. Benzoate salt of desvenlafaxine exhibits a powder X-ray diffraction pattern having peaks at about 5.81, 12.16, 13.22, 14.74, 15.66, 15.90, 16.14, 17.65, 19.40, 19.73, 19.85, 20.46, 22.42, 24.53, 24.81, 25.23, 26.65 and 28.62±0.2 degrees 2θ.

U.S. Pat. No. 6,673,838 discloses the succinate salt of desvenlafaxine and its crystalline forms.

U.S. Pat. No. 7,001,920 discloses the formate salt of desvenlafaxine. Other salts such as maleate, tartarate, aspartate and saccharinate have been described in the literature.

Polymorphism is the occurrence of different crystalline forms of a single compound and it is a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as different solubility profiles, different melting point temperatures and/or different x-ray diffraction peaks. Solvent medium and mode of crystallization play very important role in obtaining a new salt or a crystalline form over the other.

The discovery of novel solid forms, including amorphous forms and crystal forms, of pharmaceutically useful compound provides a new opportunity to improve the performance characteristics of a pharmaceutical product. Novel crystalline form L of (±)-desvenlafaxine benzoate has now been discovered.

Further, the present invention also relates to pharmaceutical composition of novel crystalline form L of desvenlafaxine benzoate and one or more pharmaceutically acceptable excipient and process for preparing them.

SUMMARY OF THE INVENTION

The present invention provides a crystalline form L of desvenlafaxine benzoate and process for its preparation. The process for preparation of novel crystalline form L of desvenlafaxine benzoate comprising the steps of:
i) providing a solution of (±)-desvenlafaxine free base in a alcohol;
ii) adding benzoic acid to the solution of step (i) and heating the mixture; and
iii) isolating the solid.

DESCRIPTION OF THE INVENTION

The present invention provides a novel crystalline form L of desvenlafaxine benzoate and process for its preparation. The process for preparation of novel crystalline form L of desvenlafaxine benzoate comprising the steps of:
i) providing a solution of (±)-desvenlafaxine free base in a alcohol;
ii) adding benzoic acid to the solution of step (i) and heating the mixture; and
iii) isolating the solid.

In one aspect of the present invention (±)-desvenlafaxine free base is obtained by the processes known in the prior art.

The alcohol employed in the step (i) is selected from methanol, ethanol, n-propanol, isopropanol, n-butanol, isobutanol and tert-butanol; more preferably isopropanol and methanol.

The ratio of alcohol employed in step (i) with respect to desvenlafaxine free base is 1-10 volumes, more preferably 5 volumes.

The reaction temperature is in the range of 10-100° C., preferably at 40-75° C. The reaction mixture is stirred for 30 to 75 minutes, preferably 45 minutes.

Molar equivalents of benzoic acid employed in step (ii) with respect to desvenlafaxine free base are 0.1 to 5 equivalents, preferably 0.5 to 1.5 equivalents.

The isolation of the crystalline solid is carried out by the conventional techniques known in the prior art such as filtration, concentration, evaporation etc.

Figure 1:
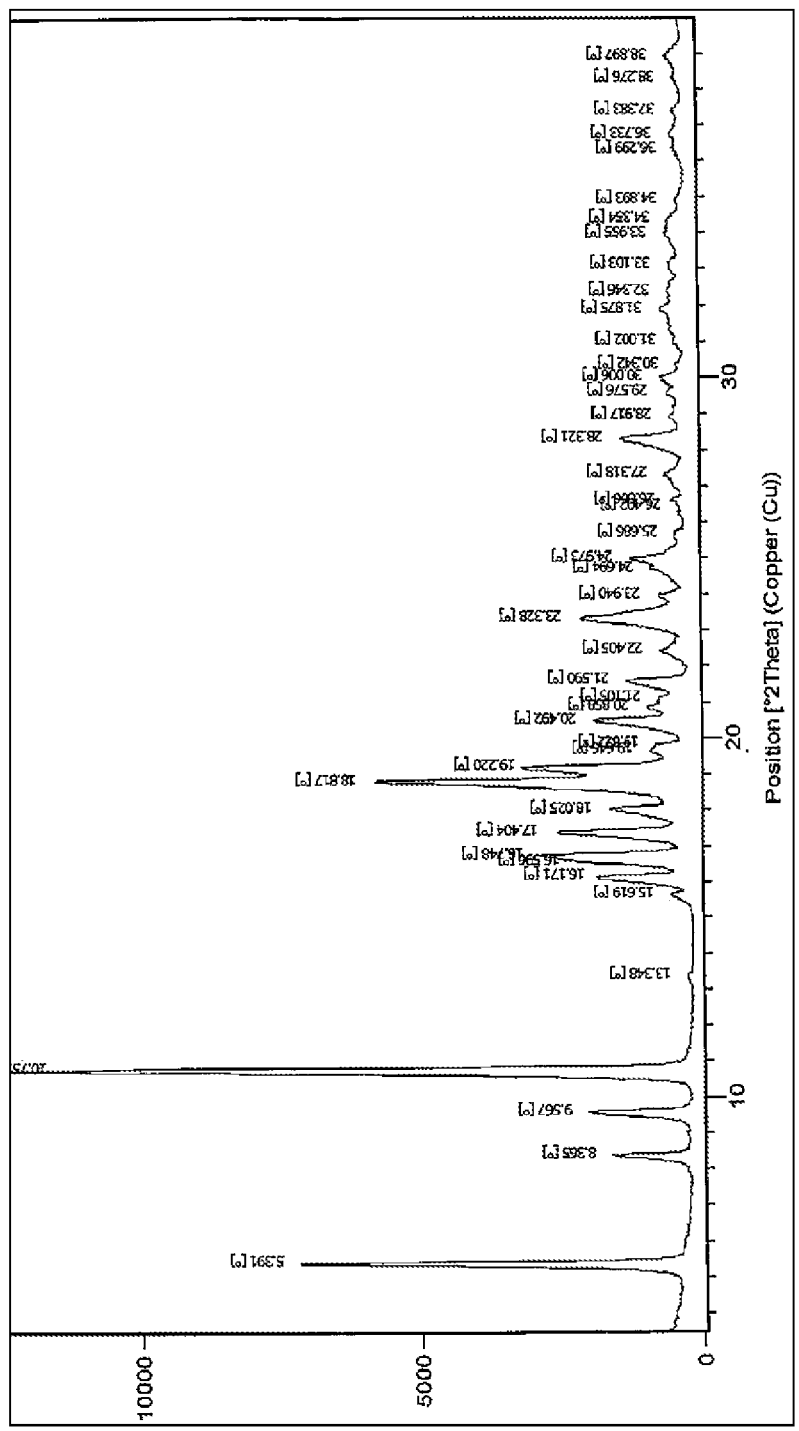
FIG. 1: illustrates characteristic powder X-ray diffraction (XRD) pattern of crystalline form L of (±)-desvenlafaxine benzoate.
Figure 2:
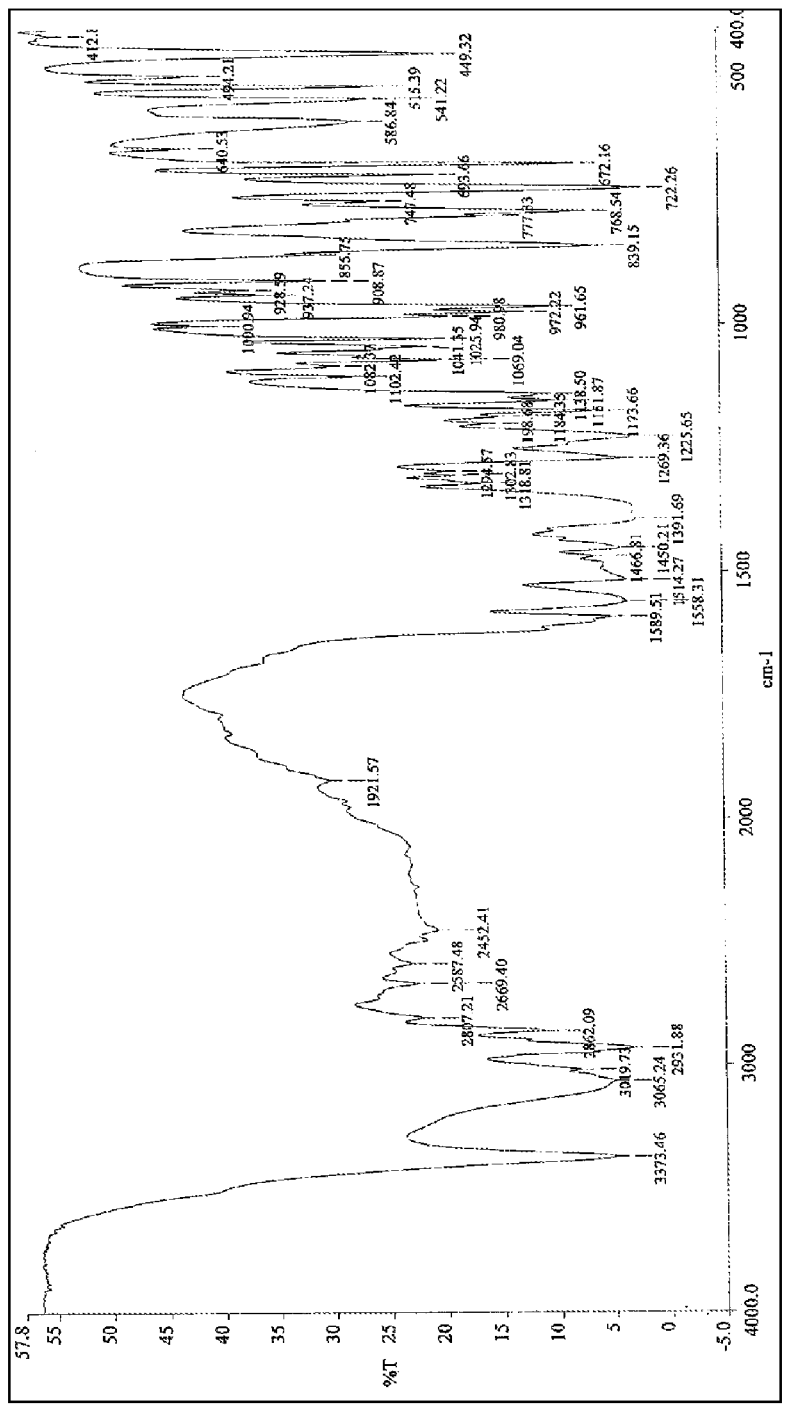
FIG. 2: illustrates IR spectrum of crystalline form L of (±)-desvenlafaxine benzoate.
Figure 3:
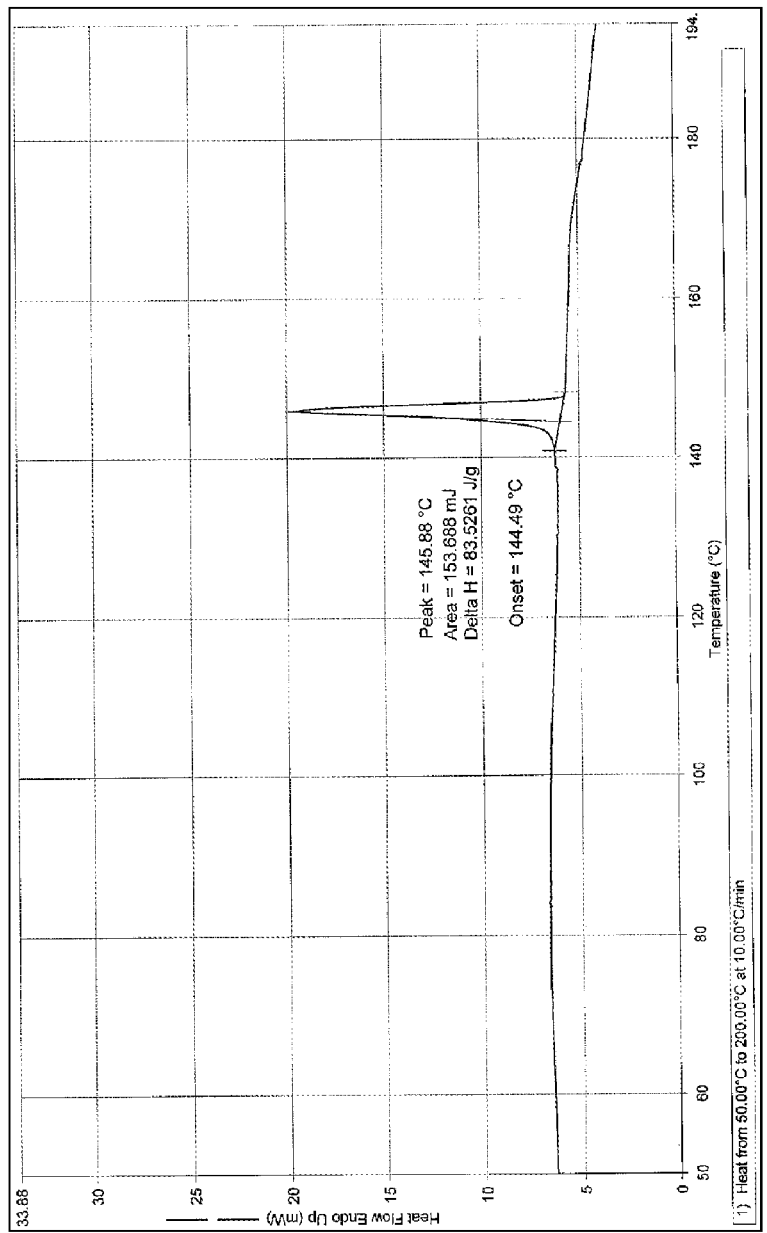
FIG. 3: illustrates differential scanning calorimetric (DSC) thermogram of crystalline form L of (±)-desvenlafaxine benzoate.
Figure 4:
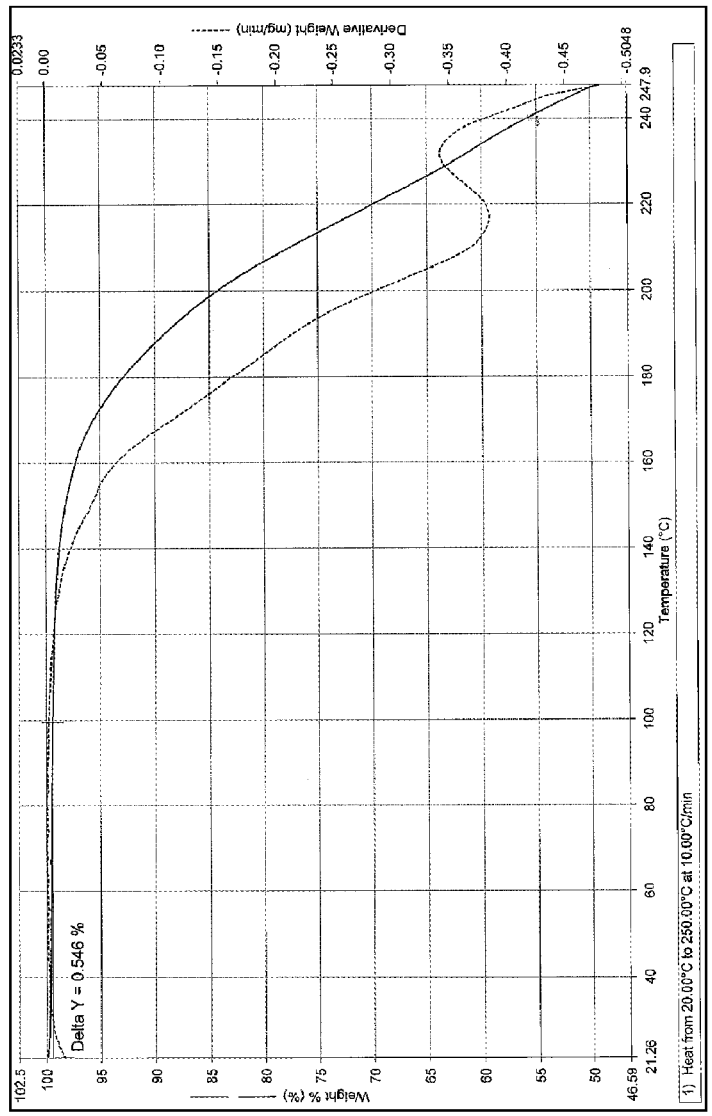
FIG. 4: illustrates thermogravimetric analysis curve (TGA) of crystalline form L of (±)-desvenlafaxine benzoate.

According to another aspect of the present invention, there is provided a solid crystalline form L of (±)-desvenlafaxine benzoate salt characterized by the following properties:

i) a powder X-ray diffraction pattern having peaks at about 5.4, 8.3, 9.5, 10.7, 16.1, 16.6, 17.3, 18.0, 18.8, 19.2, 20.4, 21.5, 23.3, 23.9, 24.9, 28.3, 29.9±0.2 degrees 2θ substantially as depicted in FIG. 1;

ii) a differential scanning calorimetric (DSC) thermogram which shows an endothermal peak at 145.88° C. as depicted in FIG. 3;

iii) melting range=147° C. to 149° C.;

iv) thermogravimetric analysis curve (TGA) obtained by heating the sample from 20 to 250° C. at a scan rate of 10° C./minute shows weight loss of 0.546% by weight as depicted in FIG. 4.

In another embodiment, a pharmaceutical composition comprising solid form L of (±)-desvenlafaxine benzoate salt disclosed herein, and one or more pharmaceutically acceptable excipient(s).

In another embodiment, a solid form L of (±)-desvenlafaxine benzoate salt disclosed herein for use in the pharmaceutical compositions of the present invention, wherein average particle size ($D_{50}$) have a size between about 5 microns to about 120 microns, preferably between about 7 microns to about 100 microns and more preferably about 10 microns to about 80 microns.

In another embodiment, a pharmaceutical composition comprising a solid form L of (±)-desvenlafaxine benzoate salt disclosed herein, wherein average particle size ($D_{50}$) have a size between about 5 microns to about 120 microns, preferably between about 7 microns to about 100 microns and more preferably about 10 microns to about 80 microns.

The terms "average particle size", "$d_{50}$" and "mass mean diameter" can be used interchangeably. The average particle size, i.e. the average equivalent diameter, is defined as the diameter where 50 mass-% of the particles of the solid form L of (±)-desvenlafaxine benzoate salt disclosed herein have a larger equivalent diameter, and the other 50 mass-% have a smaller equivalent diameter.

The "average particle size" also refers to the median particle diameter based on mass (i.e. the particle diameter where one half of the mass of particles is contributed by particles with a lesser diameter and one half of the mass of particles is contributed by particles with a greater diameter).

The particle size can be measured using methods comprising but not limited to light (eg. light-scattering methods or turbidimetric methods), sedimentation methods (eg. pipette analysis using an Andreassen pipette, sedimentation scales, photo-sedimentometers or sedimentation in a centrifugal force), pulse methods (eg. Coulter counter), or sorting by means of gravitational or centrifugal force.

It is to be understood for the purpose determining particle size of a solid form L of (±)-desvenlafaxine benzoate salt in pharmaceutical compositions, the methods comprising but not limited to isolating, crushing, extracting, separating and precipitating can be commonly employed. Determining particle size of a solid form L of (±)-desvenlafaxine benzoate salt in pharmaceutical composition is well within the scope of present invention.

A pharmaceutical composition according to the invention comprises but is not limited to tablets (single layered tablets, multilayered tablets, mini tablets, bioadhesive tablets, caplets, matrix tablets, tablet within a tablet, mucoadhesive tablets, modified release tablets, pulsatile release tablets, and timed release tablets), pellets, beads, granules, sustained release formulations, capsules, microcapsules, tablets in capsules, microspheres, matrix formulations, microencapsulation. The composition also includes immediate release as well as formulations adapted for modified, controlled, sustained, extended, or delayed release.

In another embodiment, a pharmaceutical composition of invention is a modified release composition comprising a solid form L of (±)-desvenlafaxine benzoate salt disclosed herein and one or more pharmaceutically acceptable excipient(s).

The term "modified release" used in pharmaceutical compositions of invention means controlled release, extended release, sustained release, delayed release or combination of any of these techniques. In other words, modified release pharmaceutical composition of inventions may be any formulation technique wherein release of a solid form L of (±)-desvenlafaxine benzoate salt from the composition is modified to occur at a slower rate than that from an immediate release composition.

The term 'pharmaceutically acceptable excipient(s)' used in pharmaceutical compositions of invention comprise but not limited to diluents, binders, pH stabilizing agents, disintegrants, surfactants, glidants and lubricants.

The amounts of excipient(s) employed will depend upon how much active agent is to be used. One excipient(s) can perform more than one function.

Binders as used in the invention comprises but are not limited to, starches such as potato starch, wheat starch, corn starch; microcrystalline cellulose such as products known under the registered trademarks Avicel, Filtrak, Heweten or Pharmacel; celluloses such as hydroxypropyl cellulose, hydroxyethyl cellulose, hydroxypropylmethyl cellulose (HPMC), ethyl cellulose, sodium carboxy methyl cellulose; natural gums like acacia, alginic acid, guar gum; liquid glucose, dextrin, povidone, syrup, polyethylene oxide, polyvinyl pyrrolidone, poly-N-vinyl amide, polyethylene glycol, gelatin, poly propylene glycol, tragacanth, combinations thereof and other materials known to one of ordinary skill in the art and mixtures thereof.

Fillers or diluents, as used in the invention comprises but not limited to confectioner's sugar, compressible sugar, dextrates, dextrin, dextrose, fructose, lactitol, mannitol, sucrose, starch, lactose, xylitol, sorbitol, talc, microcrystalline cellulose, calcium carbonate, calcium phosphate dibasic or tribasic, calcium sulphate, and the like can be used.

Lubricants as used in the invention comprises but not limited to Mg, Al, Ca or Zn stearate, polyethylene glycol, glyceryl behenate, mineral oil, sodium stearyl fumarate, stearic acid, hydrogenated vegetable oil and talc.

Glidants comprises but not limited to, silicon dioxide; magnesium trisilicate, powdered cellulose, starch, talc and tribasic calcium phosphate, calcium silicate, magnesium silicate, colloidal silicon dioxide, silicon hydrogel and other materials known to one of ordinary skill in the art.

Disintegrants comprises but not limited to starches; clays; celluloses; alginates; gums; cross-linked polymers, e.g., cross-linked polyvinyl pyrrolidone or crospovidone, e.g., POLYPLASDONE XL, cross-linked sodium carboxymethylcellulose or croscarmellose sodium, e.g., AC-DI-SOL from FMC; and cross-linked calcium carboxymethylcellulose; soy polysaccharides; and guar gum. Use of disintegrant according to the invention facilitates in the release of drug in the latter stage and thereby completely releasing the drug from the dosage form.

The pharmaceutical composition may optionally contain a surface-active agent. The preferred agent is copolymers composed of a central hydrophobic chain of polyoxypropylene (poly (propylene oxide)) and polyoxyethylene (poly (ethylene oxide)) that is well known as poloxamer. However, other agents may also be employed such as dioctyl sodium sulfosuccinate (DSS), triethanolamine, sodium lauryl sulphate (SLS), polyoxyethylene sorbitan and poloxalkol derivatives, quaternary ammonium salts or other pharmaceutically acceptable surface-active agents known to one ordinary skilled in the art.

The pharmaceutical composition can be formed by various processes known in the art but not limited to such as by dry granulation, wet granulation, melt granulation, direct compression, double compression, extrusion spheronization, layering and the like. The solvent(s) used in wet granulation include all the solvents well known in the art or the mixtures thereof.

In another embodiment, a pharmaceutical composition of invention comprises one or more coating comprising but not limited to modified release coating, sustained release coating, extended release coating, enteric coating, partial enteric coating or leaky enteric coating, bioadhesive coating and similar coatings known in the art. These coatings may help the pharmaceutical composition to release the drug at and for the required time. These coatings comprise coating agent(s) selected from hydrophilic or hydrophobic agent(s) or the combinations thereof.

The hydrophobic agent(s) in the coating comprises but not limited to Ammonio methacrylate copolymers type A and B as described in USP, methacrylic acid copolymer type A, B and C as described in USP, Polyacrylate dispersion 30% as described in pH. Eur., Polyvinyl acetate dispersion, ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly (ethyl methacrylate), poly(butyl methacrylate), poly(isobutyl methacrylate), and poly(hexyl methacrylate). Poly(isodecyl methacrylate), poly(lauryl methacrylate), poly(phenyl methacrylate), poly(methyl acrylate), poly(isopropyl acrylate), poly(isobutyl actylate), poly(octadecyl acrylate), waxes such as beeswax, carnauba wax, microcrystalline wax, and ozokerite; fatty alcohols such as cetostearyl alcohol, stearyl alcohol; cetyl alcohol and myristyl alcohol; and fatty acid esters such as glyceryl monostearate, glycerol distearate; glycerol monooleate, acetylated monoglycerides, tristearin, tripalmitin, cetyl esters wax, glyceryl palmitostearate, glyceryl behenate, and hydrogenated castor oil.

The hydrophilic agent(s) in the coating comprises but not limited to celluloses or their salts or derivatives thereof, hydroxyethylcellulose, hydroxypropyl cellulose, hydroxypropyl methylcellulose (hypromellose), sodium carboxymethyl cellulose, alginic acid or their salts and derivatives thereof, carbomer (Carbopol™), polyethyleneoxide, xanthan gum, guar gum, locust bean gum, poly vinyl acetate, polyvinyl alcohol, lactose, PVA these hydrophilic polymers also act as pore forming agent.

These coating comprises one or more excipients selected from the group comprising coating agents, opacifiers, taste-masking agents, fillers, polishing agents, colouring agents, antitacking agents and the like.

The pharmaceutical composition can be coated by a wide variety of methods. Suitable methods include compression coating, coating in a fluidized bed or a pan and hot melt (extrusion) coating. Such methods are well known to those skilled in the art.

In another embodiment, a stable pharmaceutical composition comprising a solid form L of (±)-desvenlafaxine benzoate salt disclosed herein, one or more pharmaceutically acceptable excipient(s) thereof.

In another embodiment of the invention is a method of lowering the incidence of nausea, vomiting, diarrhea, abdominal pain, headache, vaso-vagal malaise, and/or trismus resulting from the oral administration of a solid form L of (±)-desvenlafaxine benzoate salt disclosed herein to a patient. The method includes orally administering to a patient in need thereof a therapeutically effective amount of a sustained release oral dosage form comprising a solid form L of (±)-desvenlafaxine benzoate salt disclosed herein having a peak blood plasma level of less than about 225 ng/ml.

A solid form L of (±)-desvenlafaxine benzoate salt disclosed herein may also be provided in combination with venlafaxine. The dosage of venlafaxine is preferably about 75 mg to about 350 mg/day and more preferably about 75 mg to about 225 mg/day. Still more preferably the dosage of venlafaxine is about 75 mg to about 150 mg/day. The ratio of Desvenlafaxine to venlafaxine will vary from patient to patient depending upon a patient's response rate, but generally will be at least 6:1 Desvenlafaxine to venlafaxine.

A pharmaceutical composition of the present invention can be used to treat or prevent central nervous system disorders including, but not limited to depression (including but not limited to major depressive disorder, bipolar disorder and dysthymia), fibromyalgia, anxiety, panic disorder, agoraphobia, post traumatic stress disorder, premenstrual dysphoric disorder (also known as premenstrual syndrome), attention deficit disorder (with and without hyperactivity), obsessive compulsive disorder (including trichotillomania), social anxiety disorder, generalized anxiety disorder, autism, schizophrenia, obesity, anorexia nervosa, bulimia nervosa, Gilles de la Tourette Syndrome, vasomotor flushing, cocaine and alcohol addiction, sexual dysfunction, (including premature ejaculation), borderline personality disorder, chronic fatigue syndrome, incontinence (including fecal incontinence, overflow incontinence, passive incontinence, reflex incontinence, stress urinary incontinence, urge incontinence, urinary exertional incontinence and urinary incontinence), pain (including but not limited to migraine, chronic back pain, phantom limb pain, central pain, neuropathic pain such as diabetic neuropathy, and postherpetic neuropathy), Shy Drager can also be used for preventing relapse or recurrence of depression; to treat cognitive impairment; for the inducement syndrome, Raynaud's syndrome, Parkinson's Disease, epilepsy, and others. Compounds and compositions of the present invention of cognitive enhancement in patient suffering from senile dementia, Alzheimer's disease, memory loss, amnesia and amnesia syndrome; and in regimens for cessation of smoking or other tobacco uses. Additionally, compounds and compositions of the present invention can be used for treating hypothalamic amenorrhea in depressed and non-depressed human females.

The invention is further illustrated by following examples, which should not be construed as limiting scope of invention.

EXAMPLES

The X-ray diffraction patterns were measured using Philips X'Pertpro machine with following measurement parameters:
Scan axis: Gonio
Step size: 0.0080°
Scan type: continuous
Divergence slit size: 0.2393°
Anode material: Cu
K-Alpha 1[A°]: 1.54060

K-Alpha 2[A°]: 1.54443
K-Beta [A°]: 1.39225
Scan: 3.49 to 40° 2θ
Spinning: Yes
Measurement temperature: 25° C.

Example 1

Preparation of Crystalline Form L of (±)-Desvenlafaxine Benzoate (±)-Desvenlafaxine free base (25.0 g) was dissolved in methanol (125 ml) at 25-30° C. The solution was stirred for 5-10 minutes and benzoic acid (12.81 g) was added to the solution at 25-30° C. The reaction mixture was heated to 40-45° C. for 30-45 minutes. The reaction mixture was allowed to cool to room temperature and methanol was distilled out. To the obtained mass isopropanol was added and the reaction mixture was heated to 40-45° C. for 30-45 minutes. Reaction mixture was cooled and the crystalline solid obtained was filtered and dried under vacuum.

Yield=28 gm
% yield=75%

Example 2

Preparation of Crystalline Form L of (±)-Desvenlafaxine Benzoate (±)-Desvenlafaxine free base (25.0 g) was dissolved in isopropanol (125 ml) at 25-30° C. The solution was stirred for 5-10 minutes and benzoic acid (12.81 g) was added to the solution at 25-30° C. The reaction mixture was heated to 70-75° C. for 30-45 minutes. Activated carbon was added to the reaction mass, stirred and filtered. The product obtained was dried under vacuum.

Yield=30 gm
% yield=80%

The invention claimed is:

1. A crystalline form L of (±)-desvenlafaxine benzoate.

2. A crystalline form L of (±)-desvenlafaxine benzoate of claim 1, characterized by a powder X-ray diffraction pattern having peaks at about 5.4, 8.3, 9.5, 10.7, 16.1, 16.6, 17.3, 18.0, 18.8, 19.2, 20.4, 21.5, 23.3, 23.9, 24.9, 28.3, 29.9±0.2 degrees 2θ.

3. A crystalline form L of (±)-desvenlafaxine benzoate of claim 1, characterized by differential scanning calorimetric (DSC) thermogram which shows an endothermal peak at 145.88° C.

4. A process for preparation of crystalline form L of (±)-desvenlafaxine benzoate comprising the steps of:
   i) providing a solution of (±)-desvenlafaxine free base in a alcohol;
   ii) adding benzoic acid to the solution of step (i) and heating the mixture; and
   iii) isolating the solid.

5. The process according to claim 4, wherein the alcohol used in step (i) is selected from methanol, ethanol, n-propanol, isopropanol, n-butanol, isobutanol and tert-butanol.

6. The process according to claim 4, wherein the alcohol used in step (i) is methanol or isopropanol.

7. The process according to claim 4, wherein the step (ii) is carried out a temperature range of 10-100° C.

8. The process according to claim 4, wherein the molar ratio of benzoic acid with respect to (±)-desvenlafaxine free base is in the range of 0.1 to 5 equivalents.

9. A pharmaceutical composition comprising crystalline form L of (±)-desvenlafaxine benzoate according to claim 1, and one or more pharmaceutically acceptable excipient(s).

10. A composition comprising effective amount of crystalline form L of (±)-desvenlafaxine benzoate according to claim 1 adapted for treating a patient suffering from depression.

* * * * *